US006666827B2

United States Patent
Narimatsu

(10) Patent No.: US 6,666,827 B2
(45) Date of Patent: Dec. 23, 2003

(54) ARTERIOSCLEROSIS EVALUATING APPARATUS

(75) Inventor: Kiyoyuki Narimatsu, Komaki (JP)

(73) Assignee: Colin Corporation, Komaki (JP)

( * ) Notice: Subject to any disclaimer, the term of this patent is extended or adjusted under 35 U.S.C. 154(b) by 9 days.

(21) Appl. No.: 10/193,986

(22) Filed: Jul. 15, 2002

(65) Prior Publication Data

US 2003/0120158 A1 Jun. 26, 2003

(30) Foreign Application Priority Data

Dec. 25, 2001 (JP) ...................... 2001-390840

(51) Int. Cl.[7] ............................................... A61B 5/02
(52) U.S. Cl. ...................... 600/490; 600/500; 600/494; 600/485
(58) Field of Search .................. 600/490, 481, 600/483, 485, 492, 493, 494, 495, 496, 500, 501, 502

(56) References Cited

U.S. PATENT DOCUMENTS 5,265,011 A  * 11/1993 O'Rourke ................... 600/485
6,612,993 B2 *  9/2003 Narimatsu .................. 600/500

* cited by examiner

Primary Examiner—Max F. Hindenburg
Assistant Examiner—Navin Natnithithadha
(74) Attorney, Agent, or Firm—Oliff & Berridge, PLC

(57) ABSTRACT

An apparatus for evaluating arteriosclerosis of a living subject, including a pulse-wave detecting device which detects a pulse wave from each of a first portion and a second portion of the subject, each of the respective pulse waves detected from the first and second portions containing an incident-wave component, an augmentation-index determining device for determining, based on the pulse wave detected from the first portion by the pulse-wave detecting device, a first augmentation index indicative of a degree of augmentation of an amplitude of the pulse wave detected from the first portion, from an amplitude of the incident-wave component of the pulse wave detected from the first portion, and determining, based on the pulse wave detected from the second portion by the pulse-wave detecting device, a second augmentation index indicative of a degree of augmentation of an amplitude of the pulse wave detected from the second portion, from an amplitude of the incident-wave component of the pulse wave detected from the second portion, and an arteriosclerosis evaluating device for evaluating the arteriosclerosis of the subject, based on a comparison of the first and second augmentation indexes determined by the augmentation-index determining device.

10 Claims, 11 Drawing Sheets

ARTERIOSCLEROSIS EVALUATING APPARATUS

BACKGROUND OF THE INVENTION

1. Field of the Invention

The present invention relates to an arteriosclerosis evaluating apparatus for evaluating arteriosclerosis based on augmentation index.

2. Related Art Statement

Augmentation index, AI, is generally calculated as a percentage of a value obtained by deriving a difference between a magnitude of a peak of a pulse wave (i.e., a pulse pressure of the pulse wave) and a magnitude of a peak of an incident-wave component contained in the pulse wave (i.e., a pulse pressure of the incident wave), by the pulse pressure of the pulse wave. Since the augmentation index increases as arteriosclerosis advances, the augmentation index can be used as an index for evaluating arteriosclerosis.

However, the augmentation index is influenced by physiological factors, such as blood pressure or psychological stress, and environmental factors such as temperature, and accordingly the augmentation index may largely change between different living subjects, or between different measuring operations. Thus, a correlation between augmentation index and arteriosclerosis is not so high. Therefore, it is understood that arteriosclerosis cannot be evaluated based on augmentation index only.

SUMMARY OF THE INVENTION

It is therefore an object of the present invention to provide an arteriosclerosis evaluating apparatus for evaluating arteriosclerosis of a living subject, with high accuracy, based on augmentation index.

To achieve the above object, the Inventor has carried out extensive studies, and found the following facts: It is known that as arteriosclerosis advances, respective waveforms of respective pulse waves detected from different portions of a living subject become more and more similar to each other. Based on this knowledge, the Inventor have found that as arteriosclerosis advances, respective augmentation indexes calculated from the respective waveforms of the respective pulse waves gradually approach each other, and that arteriosclerosis can be evaluated by comparing the respective augmentation indexes of the different portions of the subject, with each other. Since those augmentation indexes are subject to common physiological changes and common environmental factors, arteriosclerosis can be evaluated with high accuracy by comparing those augmentation indexes with each other. The present invention has been developed based on these findings.

The above object has been achieved by the present invention. According to a first aspect of the present invention, there is provided an apparatus for evaluating arteriosclerosis of a living subject, comprising a pulse-wave detecting device which detects a pulse wave from each of a first portion and a second portion of the subject, each of the respective pulse waves detected from the first and second portions containing an incident-wave component; an augmentation-index determining means for determining, based on the pulse wave detected from the first portion by the pulse-wave detecting device, a first augmentation index indicative of a degree of augmentation of an amplitude of the pulse wave detected from the first portion, from an amplitude of the incident-wave component of the pulse wave detected from the first portion, and determining, based on the pulse wave detected from the second portion by the pulse-wave detecting device, a second augmentation index indicative of a degree of augmentation of an amplitude of the pulse wave detected from the second portion, from an amplitude of the incident-wave component of the pulse wave detected from the second portion; and an arteriosclerosis evaluating means for evaluating the arteriosclerosis of the subject, based on a comparison of the first and second augmentation indexes determined by the augmentation-index determining means.

According to this invention, the augmentation-index, determining means determines the respective augmentation indexes of the different portions of the living subject, and the arteriosclerosis evaluating means evaluates arteriosclerosis of the subject, based on the comparison of those augmentation indexes of the different portions. That is, since the present apparatus evaluates arteriosclerosis by comparing the plurality of augmentation indexes obtained from the single subject, with each other, the physiological changes and the environmental factors that influence those augmentation indexes are offset, and accordingly the arteriosclerosis can be evaluated with higher accuracy than the evaluation of arteriosclerosis based on a single augmentation index only.

Preferably, the arteriosclerosis evaluating apparatus further comprises a comparison-value calculating means for calculating a comparison value as the comparison of the first and second augmentation indexes determined by the augmentation-index determining means, and the arteriosclerosis evaluating means evaluates the arteriosclerosis of the subject, based on the comparison value calculated by the comparison-value calculating means and at least one of the first and second augmentation indexes determined by the augmentation-index determining means.

According to this feature, arteriosclerosis can be evaluated with improved accuracy, because at least one augmentation index itself is taken into account in addition to the comparison value as the comparison of the first and second augmentation indexes of the different portions of the living subject.

Preferably, the arteriosclerosis evaluating apparatus further comprises a comparison-value calculating means for calculating a comparison value as the comparison of the first and second augmentation indexes determined by the augmentation-index determining means; and a pulse-wave-propagation-velocity-related-information obtaining device which obtains pulse-wave-propagation-velocity-related information that is related to a velocity at which the pulse wave propagates in the subject, and the arteriosclerosis evaluating means evaluates the arteriosclerosis of the subject, based on the comparison value calculated by the comparison-value calculating means and the pulse-wave-propagation-velocity-related information obtained by the pulse-wave-propagation-velocity-related-information obtaining device.

According to this feature, arteriosclerosis can be evaluated with improved accuracy, because the pulse-wave-propagation-velocity-related information that is, like augmentation index, an index indicative of arteriosclerosis is taken into account in addition to the comparison value as the comparison of the first and second augmentation indexes of the different portions of the living subject.

Preferably, the arteriosclerosis evaluating apparatus further comprises a comparison-value calculating means for calculating a comparison value as the comparison of the first and second augmentation indexes determined by the augmentation-index determining means; and a pulse-pressure determining means for determining a pulse pressure of at least one of the respective pulse waves detected from the first and second portions by the pulse-wave detecting device, and the arteriosclerosis evaluating means evaluates the arteriosclerosis of the subject, based on the comparison value calculated by the comparison-value calculating means and the pulse pressure determined by the pulse-pressure determining means.

According to this feature, arteriosclerosis can be evaluated with improved accuracy, because the pulse pressure that is indicative of arteriosclerosis is taken into account in addition to the comparison value as the comparison of the first and second augmentation indexes of the different portions of the living subject.

According to a second aspect of the present invention, there is provided an apparatus for evaluating arteriosclerosis of a living subject, comprising a pulse-wave detecting device which detects a pulse wave from each of a first portion and a second portion of the subject, each of the respective pulse waves detected from the first and second portions containing an incident-wave component; an augmentation-index determining means for determining, based on the pulse wave detected from the first portion by the pulse-wave detecting device, a first augmentation index indicative of a degree of augmentation of an amplitude of the pulse wave detected from the first portion, from an amplitude of the incident-wave component of the pulse wave detected from the first portion, and determining, based on the pulse wave detected from the second portion by the pulse-wave detecting device, a second augmentation index indicative of a degree of augmentation of an amplitude of the pulse wave detected from the second portion, from an amplitude of the incident-wave component of the pulse wave detected from the second portion; and a display device which displays the first and second augmentation indexes determined by the augmentation-index determining means.

According to this invention, the augmentation-index determining means determines the respective augmentation indexes of the different portions of the living subject, and the display device displays the respective augmentation indexes of the different portions. Thus, a person can judge, from comparison of the respective augmentation indexes displayed, that the nearer those augmentation index values are to each other, the higher the degree of arteriosclerosis is; and that the more distant the augmentation index values are from each other, the lower the degree of arteriosclerosis is. Thus, arteriosclerosis can be evaluated with higher accuracy than the evaluation of arteriosclerosis based on a single augmentation index only.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
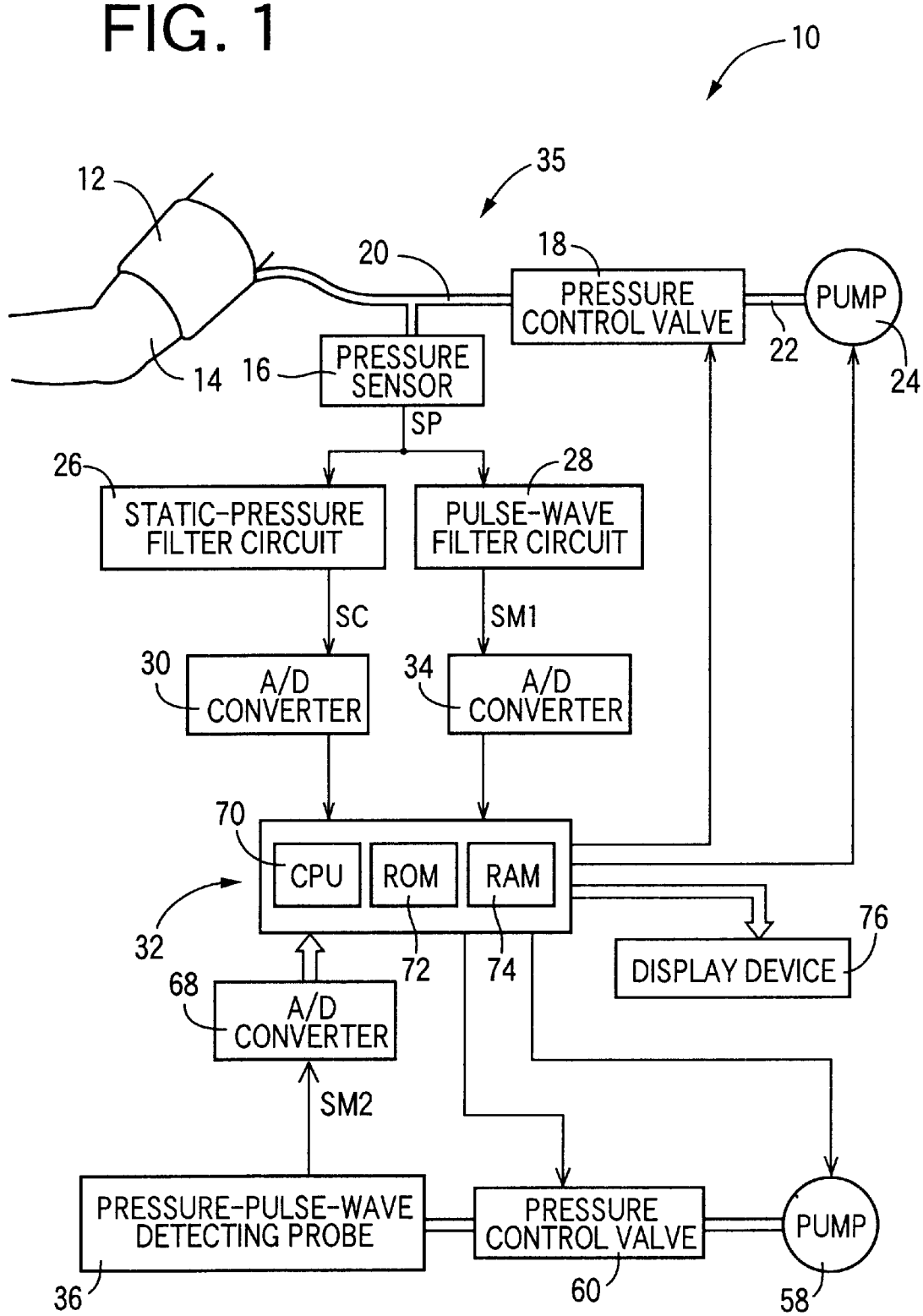
FIG. 1 is a diagrammatic view showing a circuitry of an arteriosclerosis evaluating apparatus to which the present invention is applied.

Hereinafter, there will be described embodiments of the present invention in detail by reference to the drawings. FIG. 1 is a diagrammatic view showing a circuitry of an arteriosclerosis evaluating apparatus 10 to which the present invention is applied.

In FIG. 1, the present apparatus includes an inflatable cuff 12 which includes a belt-like cloth bag and a rubber bag accommodated in the cloth bag and which is wound around, e.g., a right upper arm 14 of a living subject. The cuff 12 is connected to a pressure sensor 16 and a pressure control valve 18 via a piping 20. The pressure control valve 18 is connected to an air pump 24 via a piping 22. The pressure control valve 18 adjusts a pressure of a pressurized air supplied from the air pump 24, and supplies the pressure-adjusted air to the cuff 12, or discharges the air from the cuff 12, thereby controlling an air pressure in the cuff 12.

The pressure sensor 16 detects the air pressure in the cuff 12, and supplies a pressure signal SP representing the detected pressure, to each of a static-pressure filter circuit 26 and a pulse-wave filter circuit 28. The static-pressure filter circuit 26 includes a low-pass filter and extracts, from the pressure signal SP, a static-pressure component contained in the pressure signal SP, i.e., a cuff-pressure signal SC representing the static pressure in the cuff 12 (hereinafter, referred to as the cuff pressure PC). The cuff-pressure signal SC is supplied to an electronic control device 32 via an A/D (analog-to-digital) converter 30. The pulse-wave filter circuit 28 includes a band-pass filter and extracts, from the pressure signal SP, an oscillatory component, i.e., a cuff-pulse-wave signal SM1. The cuff-pulse-wave signal SM1 is supplied to the control device 32 via an A/D converter 34. The cuff-pulse-wave signal SM1 represents a brachial pulse wave wb that is produced from a brachial artery, not shown, of the subject, pressed by the cuff 12. Thus, the cuff 12, the pressure sensor 16, the pulse-wave filter circuit 28, etc.

cooperate with one another to provide a brachial-pulse-wave detecting device 35.

Figure 2:
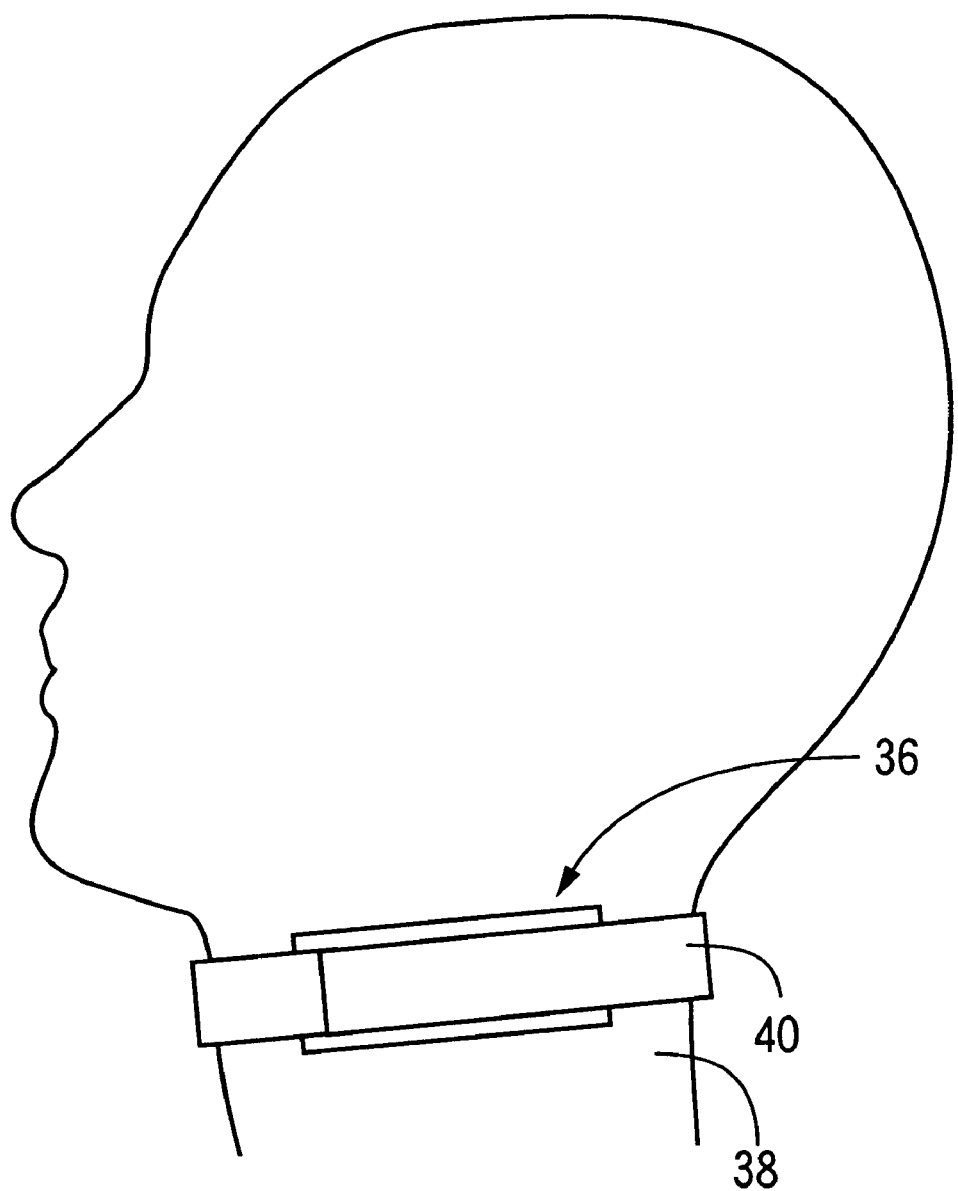
FIG. 2 is an illustrative view showing a state in which a pressure-pulse-wave detecting probe of the arteriosclerosis evaluating apparatus of FIG. 1 is worn on a neck portion of a living subject.
Figure 3:
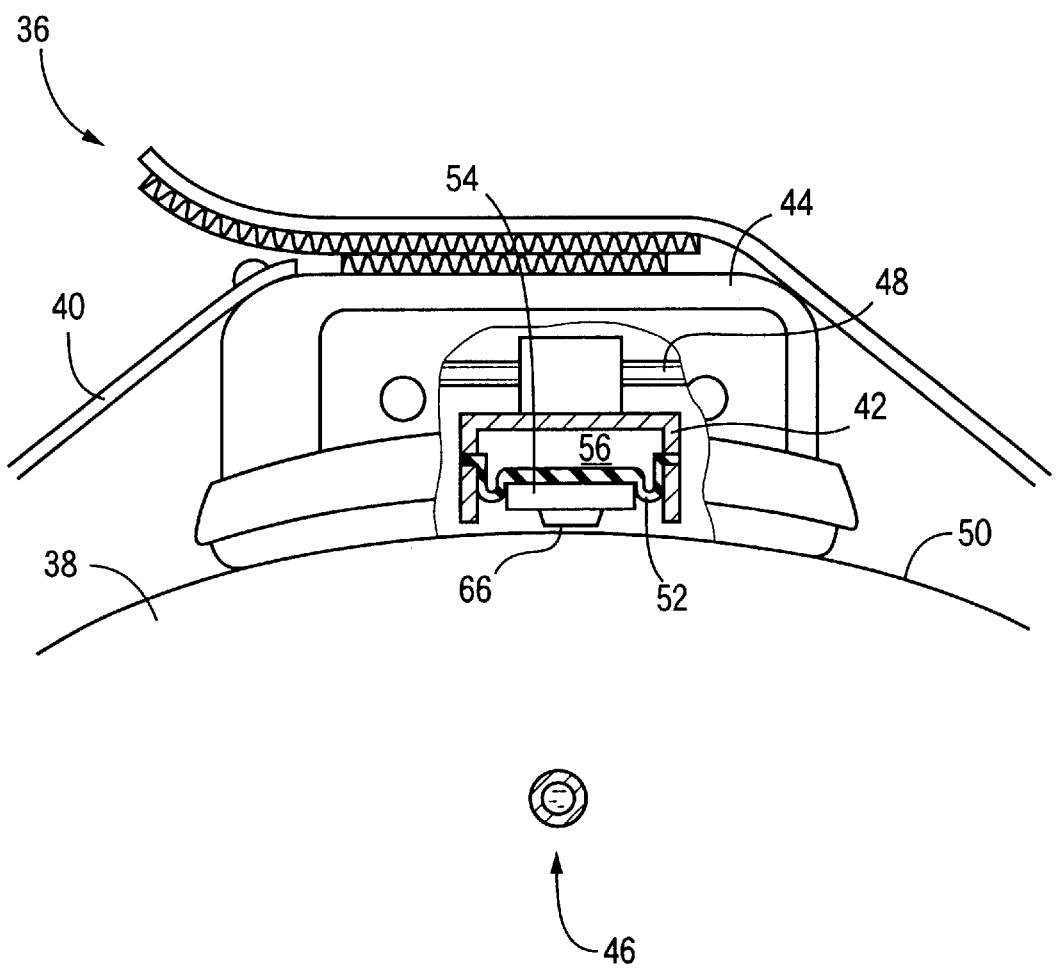
FIG. 3 is an enlarged view of the pressure-pulse-wave detecting probe of FIG. 2, a portion of the probe being cut away.

The present arteriosclerosis evaluating apparatus 10 additionally includes a pressure-pulse-wave detecting probe 36, shown in FIG. 2, functioning as a carotid-pulse-wave detecting device. The pressure-pulse-wave detecting probe 36 is worn on a neck portion 38 of the subject, with the help of a band 40, as illustrated in FIG. 2. As shown in detail in FIG. 3, the pressure-pulse-wave detecting probe 36 includes a container-like sensor housing 42; a case 44 which accommodates the sensor housing 42; and a feed screw 48 which is threadedly engaged with the sensor housing 42 and is rotated by an electric motor, not shown, provided in the case 44 so as to move the sensor housing 42 in a widthwise direction of a carotid artery 46. The pressure-pulse-wave detecting probe 36 is detachably attached to the neck portion 38, such that an open end of the sensor housing 42 is opposed to a body surface 50 of the neck portion 38.

In addition, the pressure-pulse-wave detecting probe 36 includes a pressure-pulse-wave sensor 54 which is secured via a diaphragm 52 to an inner wall of the sensor housing 42, such that the sensor 54 is movable relative to the housing 42 and is advanceable out of the open end of the same 42. The sensor housing 42, the diaphragm 52, etc. cooperate with one another to define a pressure chamber 56, which is supplied with a pressurized air from an air pump 58 via a pressure-control valve 60, as shown in FIG. 1, so that the pressure-pulse-wave sensor 54 is pressed against the body surface 50 with a pressing force corresponding to the air pressure (Pa) in the pressure chamber 56.

The sensor housing 42 and the diaphragm 52 cooperate with each other to provide a pressing device 62 which presses the pressure-pulse-wave sensor 54 against the carotid artery 46, and the feed screw 48 and the not-shown motor cooperate with each other to provide a widthwise-direction moving device 64 which moves the pressure-pulse-wave sensor 54 in the widthwise direction of the carotid artery 46 and thereby changes a pressing position where the sensor 54 is pressed on the body surface 50.

Figure 4:
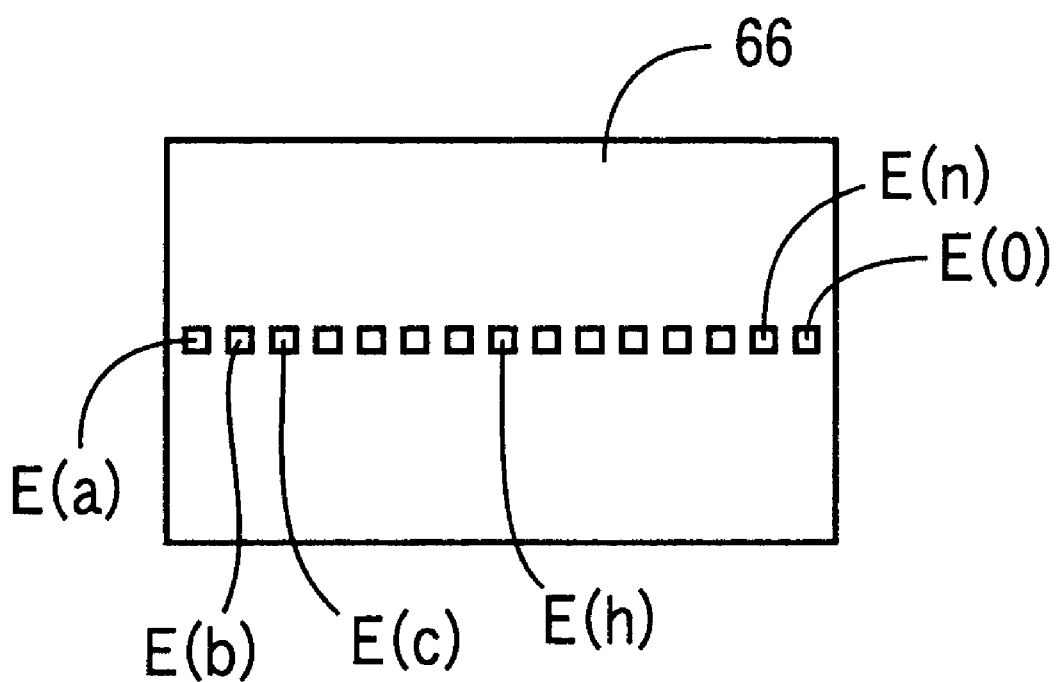
FIG. 4 is a view for explaining a state in which an array of pressure-sensing elements is provided in a press surface of a pressure-pulse-wave sensor shown in FIG. 3.

The pressure-pulse-wave sensor 54 has a pressing surface 66, and a number of semiconductor pressure-sensing elements (hereinafter, referred to as the "pressure-sensing elements") E which are arranged in the pressing surface 66 at a regular interval in the widthwise direction of the carotid artery 46, i.e., in the direction of movement of the pressure-pulse-wave sensor 54 parallel to the feed screw 48, over a length greater than the diameter of the carotid artery 46. For example, as shown in FIG. 4, fifteen pressure-sensing elements E(a), E(b), . . . , E(o) are arranged at a regular interval of, e.g., 0.6 mm.

The pressure-pulse-wave detecting probe 36, constructed as described above, is pressed against the body surface 50 of the neck portion 38 right above the carotid artery 46, so that the pressure-pulse-wave sensor 54 detects a pressure pulse wave (i.e., a carotid pulse wave, wc) which is produced from the carotid artery 46 and is propagated to the body surface 50, and supplies a pressure-pulse-wave signal SM2 representing the detected carotid pulse wave wc, to the control device 32 via an A/D converter 68. An example of the carotid pulse wave wc represented by the pressure-pulse-wave signal SM2 continuously supplied from the pressure-pulse-wave sensor 54 is indicated at solid line in FIG. 5.

The control device 32 is provided by a so-called microcomputer including a CPU (central processing unit) 70, a ROM (read only memory) 72, a RAM (random access memory) 74, and an I/O (input-and-output) port, not shown.

The CPU 70 processes signals according to the control programs pre-stored in the ROM 72 by utilizing the temporary-storage function of the RAM 74, and outputs, via the I/O port, respective drive signals to control the pressure control valves 24, 58 and the air pumps 18, 60 and thereby control the air pressure in the cuff 12 (i.e., the cuff pressure PC) and the air pressure in the pressure chamber 56. In addition, the CPU 70 calculates, based on the cuff-pulse-wave signal SM1 supplied from the pulse-wave filter circuit 28 and the pressure-pulse-wave signal SM2 supplied from the pressure-pulse-wave sensor 54, an augmentation index AI, etc., and additionally controls what is displayed by a display device 76.

Figure 6:
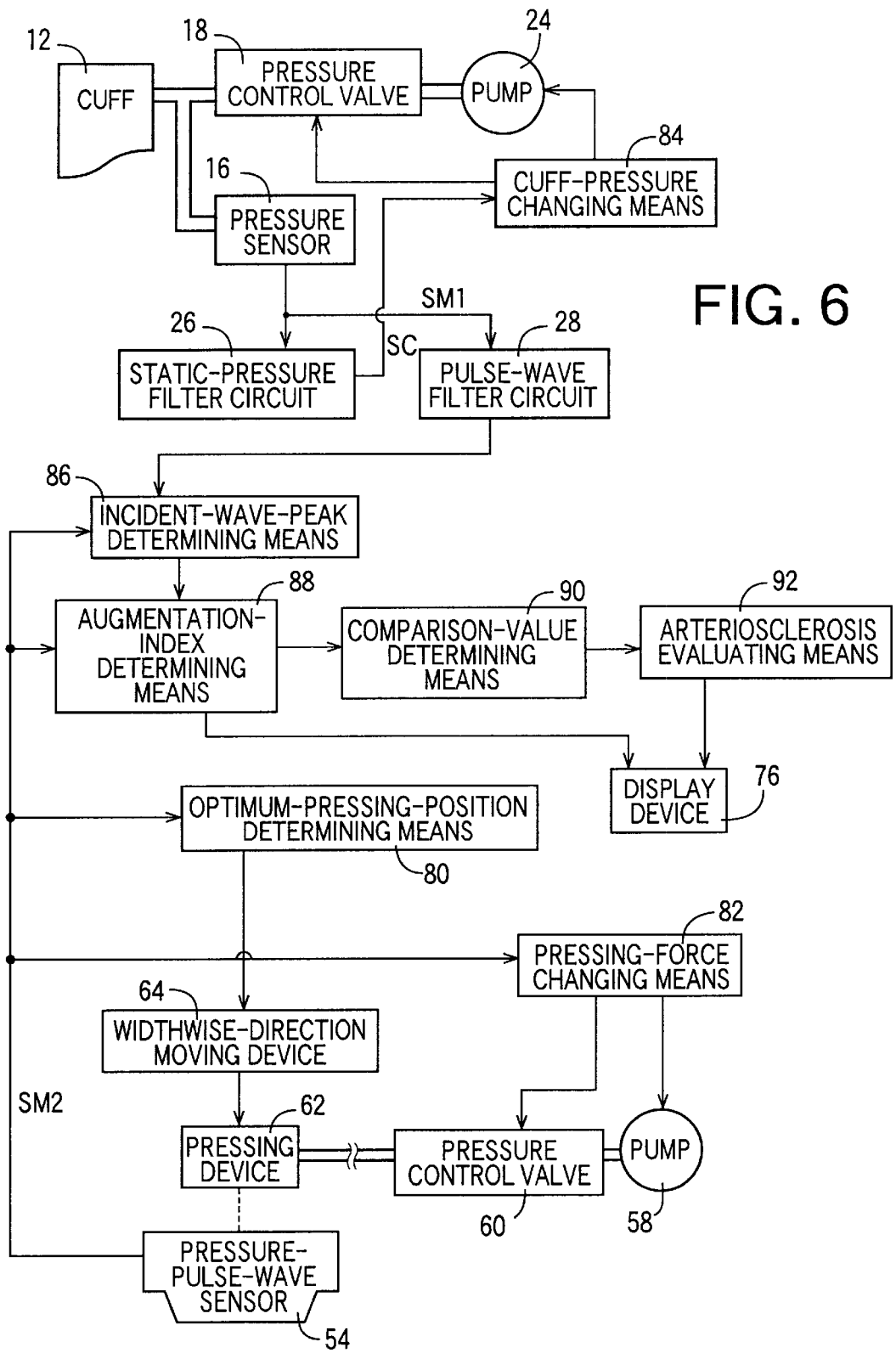
FIG. 6 is a block diagram for explaining essential control functions of an electronic control device of the arteriosclerosis evaluating apparatus of FIG. 1.

FIG. 6 is a diagrammatic view for explaining essential control functions of the control device 32 of the present arteriosclerosis evaluating apparatus 10. An optimum-pressing-position determining means 80 judges whether a prescribed pressing-position changing condition is satisfied, i.e., whether one (hereinafter, referred to as the "highest-pressure detecting element EM") of the pressure-sensing elements E of the pressure-pulse-wave sensor 54 that detects the highest pressure of the respective pressures detected by all the elements E is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. The highest-pressure detecting element EM is one of the elements E that is positioned right above the carotid artery 46. When this pressing-position changing condition is satisfied, the optimum-pressing-position determining means 80 carries out the following pressing-position changing operation: After the pressing device 62 once moves the pressure-pulse-wave sensor 54 away from the body surface 50, the widthwise-direction moving device 64 moves the pressing device 62 and the sensor 54 over a prescribed distance, and then the pressing device 62 again presses the sensor 54 with a prescribed, considerably low first pressing force HDP1. In this state, the determining means 80 judges again whether the prescribed pressing-position changing condition is satisfied. The determining means 80 repeats carrying out the above-described operation and judgment till the pressing-position changing condition is not satisfied any longer, preferably till the highest-pressure detecting element EM is positioned in a prescribed middle portion of the array of elements E. The length, or the number of elements, employed to define each of the opposite end portions of the array of elements E is prescribed based on the diameter of the artery (i.e., the carotid artery 46) to be pressed by the pressure-pulse-wave sensor 54, and may be, e.g., one fourth of the diameter.

A pressing-force changing means 82 changes, after the optimum-pressing-position determining means 80 positions the pressure-pulse-wave sensor 54 at the optimum pressing position, a pressing force HDP (i.e., a hold-down pressure) applied by the pressing device 62 to the sensor 54, within a prescribed pressing-force range, either stepwise in response to each heartbeat of the subject, or continuously at a prescribed, considerably low rate. Based on the carotid pulse wave wc obtained during the changing of the pressing force HDP, the changing means 82 determines an optimum pressing force HDPO and maintains the pressing force applied by the pressing device 62 to the sensor 54, at the thus determined optimum pressing force HDPO. Here, the optimum pressing force HDPO is so determined that a pulse pressure PPc of the carotid pulse wave wc (i.e., a value obtained by subtracting a minimal value, from a maximal value, of one heartbeat-synchronous pulse of the carotid pulse wave wc) detected by the highest-pressure detecting element EM pressed by the pressing force HDP may not be smaller than a predetermined lower-limit pulse pressure $PPc_L$. The lower-limit pulse pressure $PPc_L$ is experimentally determined as a value which assures that a clear carotid pulse wave wc is detected. If the pulse pressure PPc is too small, a clear carotid pulse wave wc is not detected.

A cuff-pressure changing means 84 controls, based on the cuff-pressure signal SC supplied from the static-pressure filter circuit 26, the air pump 24 and the pressure control valve 18 so as to change and keep the cuff pressure PC to and at a prescribed pulse-wave detecting pressure. Here, the pulse-wave detecting pressure is defined as a pressure which is lower than a diastolic blood pressure of the upper arm 14 and which assures that the cuff-pulse-wave signal SM1 extracted by the pulse-wave filter circuit 28 has a sufficiently great magnitude. The pulse-wave detecting pressure may be, e.g., 60 mmHg.

An incident-wave-peak determining means 86 successively determines an amplitude (i.e., a pulse pressure PPci), and a time of occurrence, of a peak, pci, of an incident-wave component, wci, which is contained in each of successive heartbeat-synchronous pulses of the carotid pulse wave wc continuously detected by the highest-pressure detecting element EM of the pressure-pulse-wave sensor 54 in the state in which the pressing force HDP applied to the sensor 54 is maintained at the optimum pressing force HDPO. In addition, the incident-wave-peak determining means 86 successively determines an amplitude (i.e., a pulse pressure PPbi), and a time of occurrence, of a peak, pbi, of an incident-wave component, wbi, which is contained in each of successive heartbeat-synchronous pulses of the brachial pulse wave wb continuously detected by the pulse-wave filter circuit 28 in the state in which the cuff pressure PC is maintained at the above-described pulse-wave detecting pressure. Since the peak pci of the incident wave wci of the carotid pulse wave wc and the peak pbi of the incident wave wbi of the brachial pulse wave wb are determined in an identical manner, this manner will be described below with reference to the carotid pulse wave wc as a representative of the two sorts of pulse waves wc, wb.

Figure 5:
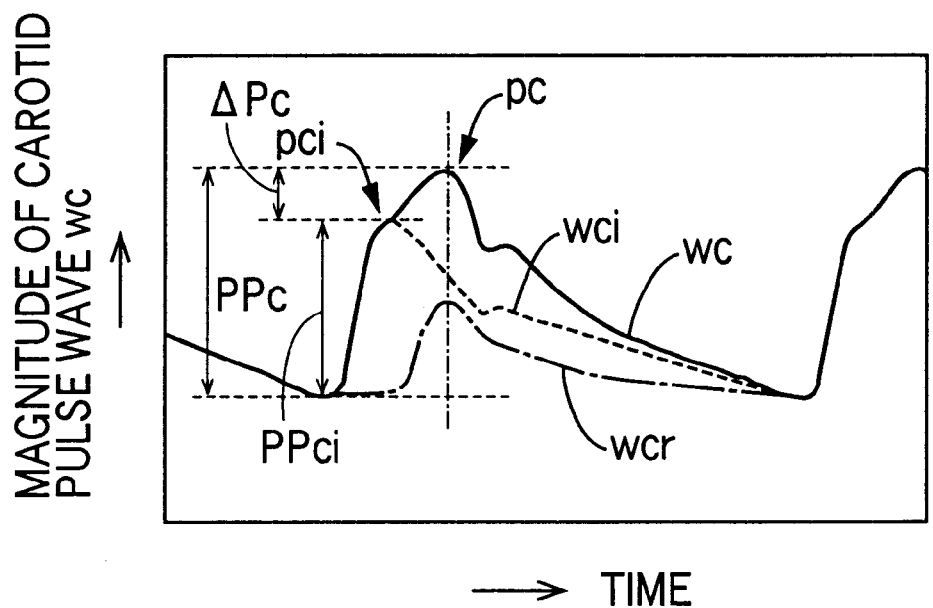
FIG. 5 is a graph showing an example of a carotid pulse wave wc represented by a pressure-pulse-wave signal SM2 supplied from a pressure-sensing element of the pressure-pulse-wave sensor of FIG. 1.

The carotid pulse wave wc contains the incident wave wci, indicated at broken line in FIG. 5, and the peak pci of the incident wave wci corresponds to an inflection point or a maximal point of the composite carotid pulse wave wc (i.e., observed wave) that occurs between a rising point and a peak point, pc, of the composite wave wc (in the example shown in FIG. 5, the peak pci of the incident wave wci corresponds to an inflection point of the observed wave wc). To this end, the incident-wave-peak determining means 86 subjects the continuously obtained pressure-pulse-wave signal SM2 to a prescribed mathematical treatment, to detect an inflection point or a maximal point occurring between a rising point and a peak point pc of each heartbeat-synchronous pulse of the carotid pulse wave wc, and determines a magnitude, and a time of occurrence, of the inflection point or the maximal point as a magnitude, and a time of occurrence, of the peak pci of the incident wave wci. Here, the mathematical treatment may be a common treatment used to detect an inflection point or a maximal point; such as a differentiation treatment or a filter treatment.

The carotid pulse wave wc contains a reflected-wave component wcr, indicated at one-dot chain line in FIG. 5.

Thus, the carotid pulse wave wc is a composite wave of a pressure wave (the incident wave wci) produced when blood is ejected from the heart of the subject and propagated in a direction toward a peripheral portion of the subject, and a reflected wave of the pressure wave, i.e., the reflected wave wcr. It is speculated that a main component of the reflected wave wr is one which is reflected around a common iliac artery of the subject.

An augmentation-index determining means 88 determines an augmentation index, AIc, indicative of a degree of augmentation of an amplitude of each heartbeat-synchronous pulse of the carotid pulse wave wc from an amplitude of an incident wave of the each pulse of the wave wc, and an augmentation index, AIb, indicative of a degree of augmentation of an amplitude of each heartbeat-synchronous pulse of the brachial pulse wave wb from an amplitude of an incident wave of the each pulse of the wave wb that is detected, preferably, at substantially the same time as the time when the each pulse of the wave wc is detected. More specifically described, the augmentation-index determining means 88 determines a carotid-artery-pulse-wave augmentation index AIc based on the carotid pulse wave wc detected by the highest-pressure detecting element EM of the pressure-pulse-wave sensor 54 in the state in which the pressing force HDP applied to the sensor 54 is maintained at the optimum pressing force HDPO, and additionally determines a brachial-artery-pulse-wave augmentation index AIb based on the brachial pulse wave wb detected by the pulse-wave filter circuit 28 in the state in which the cuff pressure PC is maintained at the pulse-wave detecting pressure. In addition, the determining means 88 controls the display device 76 to display the thus determined carotid-artery-pulse-wave augmentation index AIc and brachial-artery-pulse-wave augmentation index AIb.

An augmentation index AI, e.g., a carotid-artery-pulse-wave augmentation index AIc is usually determined as a percentage of a difference, ΔPc, of the pulse pressure PPc of the carotid pulse wave wc and the pulse pressure PPci of the incident wave wci, relative to the pulse pressure PPc, i.e., according to the following Expression 1:

$$AIc=(\Delta Pc/PPc)\times 100 \qquad\qquad \text{(Expression 1)}$$

Otherwise, the carotid-pulse-wave augmentation index AIc may be determined as a value (=PPci/PPc=PPci/(PPci+ΔPc)) obtained by dividing, by the pulse pressure PPc of the carotid pulse wave wc, the pulse pressure PPci of the incident wave wci; a value (=PPc/PPci=(PPci+ΔP)/PPci) obtained by dividing the pulse pressure PPc of the carotid pulse wave wc, by the pulse pressure PPci of the incident wave wci; a value (=ΔP/PPci) obtained by dividing the difference ΔP by the pulse pressure PPci of the incident wave wci; a value (=PPc/ΔP) obtained by dividing, by the difference ΔP, the pulse pressure PPc of the carotid pulse wave wc; a value (=PPci/ΔP) obtained by dividing, by the difference ΔP, the pulse pressure PPci of the incident wave wci; or a percentage of each of the above values. The brachial-pulse-wave augmentation index AIb is also determined as indicated above.

A comparison-value calculating means 90 calculates a comparison value by comparing the carotid-pulse-wave augmentation index AIc and the brachial-pulse-wave augmentation index AIb determined by the augmentation-index determining means 88, with each other. The comparison value may be any value that represents a relative relationship between respective magnitudes of the two indexes AIc, AIb. For example, the comparison value may be a ratio, R, of one of the two indexes AIc, AIb to the other (R=AIc/AIb or AIb/AIc); a difference, d, of one of the two indexes AIc, AIb from the other (d=AIc−AIb or AIb−AIc); or a value (=d/R) obtained by dividing the difference d by the ratio R.

As previously noted, as degree of arteriosclerosis increases, respective shapes or forms of respective pulse waves detected from respective portions of the subject becomes more similar to each other. Therefore, the comparison value changes with the degree of arteriosclerosis. For example, as the degree of arteriosclerosis increases, the ratio R approaches 1 and the difference d approaches 0.

An arteriosclerosis evaluating means 92 evaluates arteriosclerosis of the subject, based on the comparison value calculated by the comparison-value calculating means 90, and controls the display device 76 to display the result of evaluation of arteriosclerosis. The evaluation of arteriosclerosis may be a judgment about whether the subject has arteriosclerosis or not, or a determination of a degree of arteriosclerosis of the subject. In the former case, the arteriosclerosis evaluating means 92 judges that the subject has arteriosclerosis, if the comparison value determined by the comparison-value calculating means 90 falls within an arteriosclerosis range that is experimentally determined in advance. In the case where the comparison value is the ratio R, the arteriosclerosis range may be a considerably narrow range whose middle value is 1; and in the case where the comparison value is the difference d, the arteriosclerosis range may be a considerably narrow range whose middle value is 0.

In the above-indicated latter case, i.e., in the case where the arteriosclerosis evaluating means 92 determines a degree of arteriosclerosis of the subject, the ROM 72 stores, in advance, a predetermined relationship between comparison value and arteriosclerosis degree, and the arteriosclerosis evaluating means 92 determines an arteriosclerosis degree of the subject, based on the comparison value actually determined by the comparison-value calculating means 90, according to the relationship stored in the ROM 72. This relationship may be expressed by a mathematical function whose variables are comparison value and arteriosclerosis degree.

Figure 7:
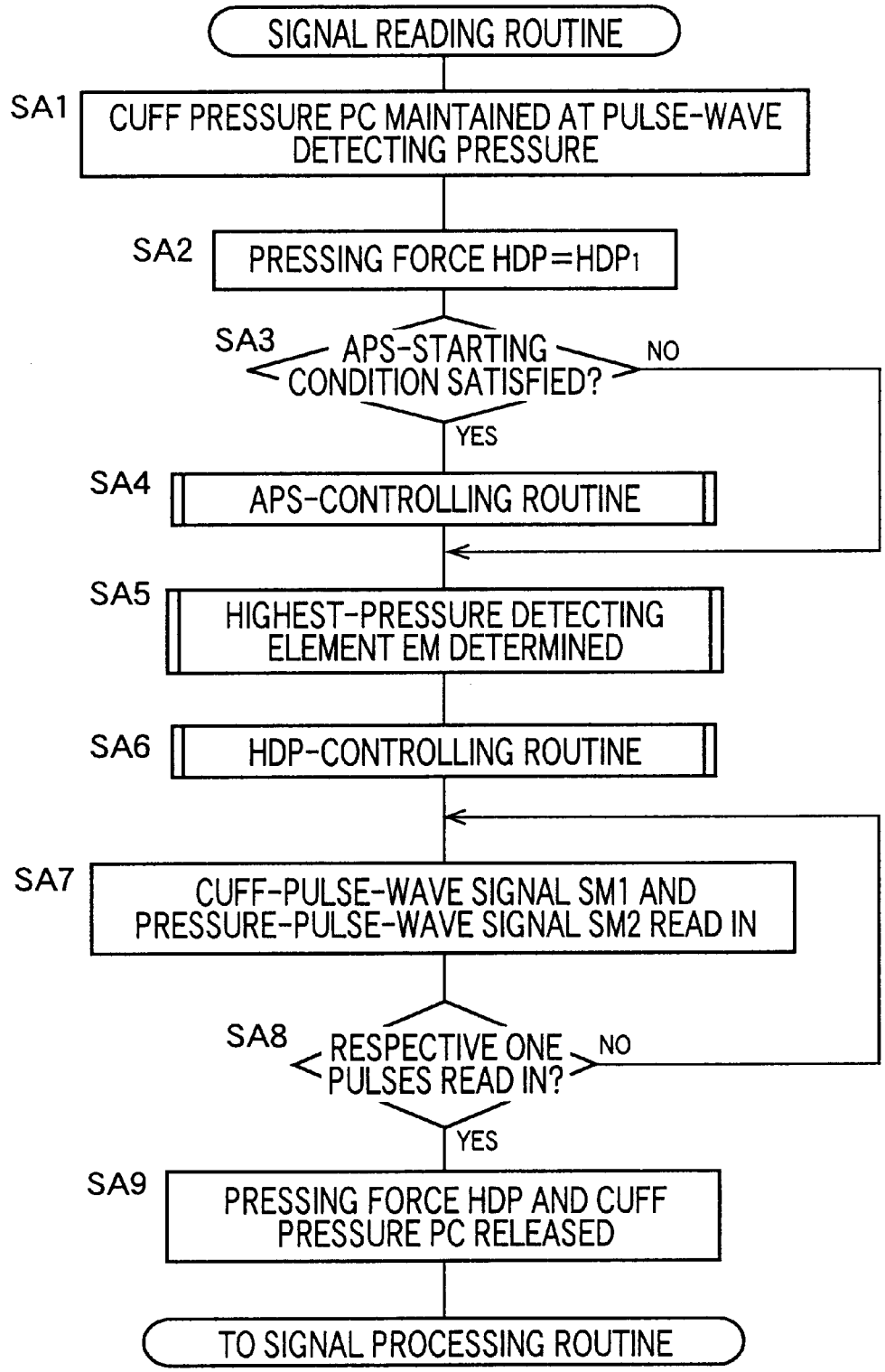
FIG. 7 is a flow chart for explaining more concretely the control functions of a CPU (central processing unit) of the control device, shown in FIG. 6, in particular, a signal reading routine.
Figure 8:
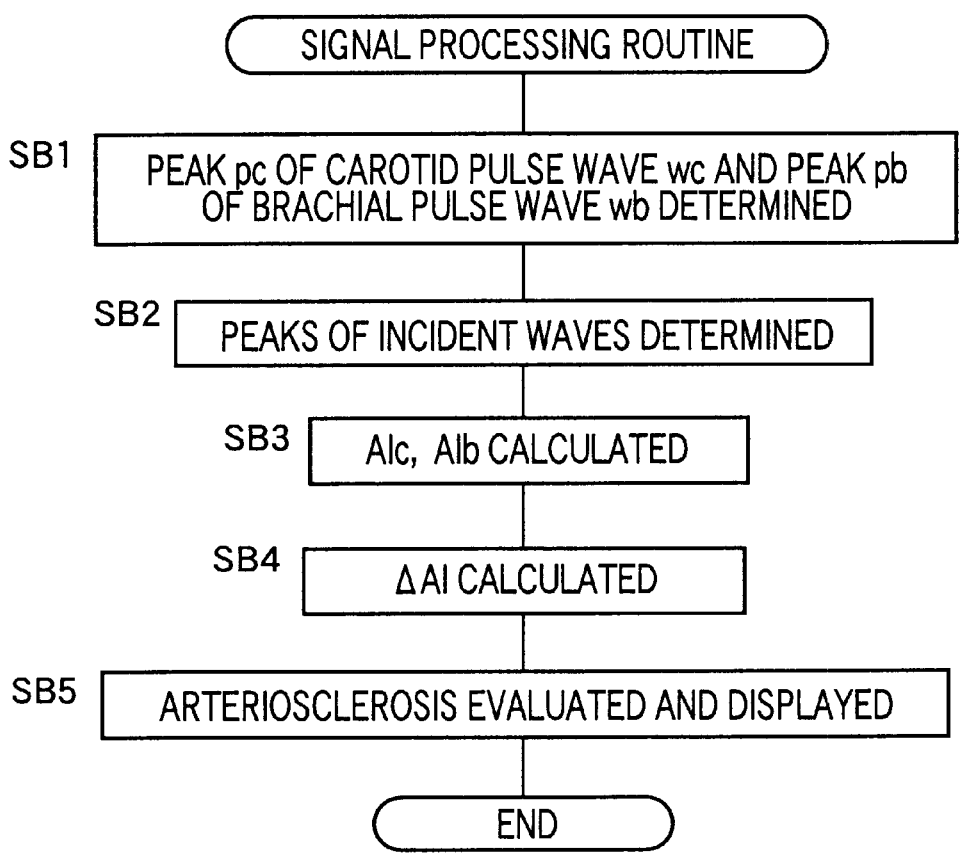
FIG. 8 is a flow chart for explaining more concretely the control functions of the CPU, shown in FIG. 6, in particular, a signal processing routine.

FIGS. 7 and 8 are flow charts representing the control functions of the CPU 70, shown in FIG. 6. FIG. 7 shows a signal reading routine for reading in the pulse-wave signals SM1, SM2; and FIG. 8 shows a signal processing routine for processing the thus read-in pulse-wave signals SM1, SM2.

In FIG. 7, first, the control device 32 carries out Step SA1 (hereinafter, the term "Step(s)" is omitted, if appropriate) where the control device starts the air pump 24 and controls the pressure control valve 18 so that the cuff pressure PC is changed to, and maintained at, the pulse-wave detecting pressure, i.e., 60 mmHg.

Subsequently, the control goes to Steps SA2 to SA4 corresponding to the optimum-pressing-position determining means 80. At SA2, the control device operates the pressing device 62 to change the pressure in the pressure chamber 56 so that the pressing force HDP applied to the pressure-pulse-wave sensor 54 is maintained at the prescribed first pressing force HDP1. The first pressing force HDP1 is experimentally determined, in advance, as a pressing force HDP which assures that respective S/N ratios of the carotid pulse waves wc detected by the pressure-sensing elements E are high enough to allow the respective peaks pc of the carotid pulse waves wc to be detected with considerably high accuracy.

Then, the control proceeds with SA3 where the control device judges whether the prescribed pressing-position changing condition (i.e., the APS-starting condition) is satisfied, i.e., whether the highest-pressure-detecting element EM as one of the pressure-sensing elements E provided in the pressing surface 66 is located in one of the prescribed opposite end portions of the array of elements E. If a negative judgment is made at SA3, the control goes to SA5 and the following steps, described later.

On the other hand, if a positive judgment is made at SA3, that is, if the pressing position where the pressure-pulse-wave sensor 54 is pressed against the carotid artery 46 is not appropriate, the control proceeds with SA4, i.e., an APS-controlling routine. According to this APS-controlling routine, the control device determines the optimum pressing position where the highest-pressure-detecting element EM is located at substantially the middle of the array of elements E. To this end, the control device carries out the following sequential operations, i.e., operates the pressing device 62 and the widthwise-direction moving device 64 to once move the pressure-pulse-wave sensor 54 off the body surface 50, move the pressing device 62 and the sensor 54 over a prescribed distance, and again press the sensor 54 with the prescribed pressing force HDP1. In this state, the control device again judges whether the highest-pressure-detecting element EM is located at substantially the middle of the array of elements E. SA3 and SA4 are repeated till a positive judgment is made at SA3.

Thus, at SA4, the control device positions the pressure-pulse-wave sensor 54 at the optimum pressing position. Then, or if a negative judgment is made at Step SA3, the control goes to SA5 where the control device selects, in this state, a new highest-pressure detecting element EM from the pressure-sensing elements E of the sensor 54. SA5 is followed by SA6 corresponding to the pressing-force changing means 82, where the control device carries out the HDP-controlling routine in which the pressing force HDP applied by the pressing device 62 to the sensor 54 is continuously increased from the first pressing force HDP1. During this increasing of the pressing force HDP, the control device determines an optimum pressing force HDPO based on a judgment about whether a pulse pressure PPc of each of successive heartbeat-synchronous pulses of the carotid pulse wave wc detected by the highest-pressure detecting element EM selected at SA5 is not smaller than a prescribed optimum pulse pressure PL. Then, the control device changes and maintains the pressing force HDP applied to the pressure-pulse-wave sensor 54, to and at the thus determined optimum pressing force HDPO.

Then, the control goes to SA7 where the control device reads in the cuff-pulse-wave signal SM1 supplied from the pulse-wave filter circuit 28 and the pressure-pulse-wave signal SM2 supplied from the highest-pressure detecting element EM of the pressure-pulse-wave sensor 54 and, then at SA8, the control device judges whether the control device has read in one heartbeat-synchronous pulse of each of the cuff-pulse-wave signal SM1 and the pressure-pulse-wave signal SM2. If a negative judgment is made at SA8, SA7 and the following steps are repeated to continue reading in the cuff-pulse-wave signal SM1 and the pressure-pulse-wave signal SM2. Meanwhile, if a positive judgment is made at SA8, then the control goes to SA9 where the control device stops the air pump 24 and controls the pressure control valve 18 so that the cuff pressure PC is decreased to atmospheric pressure, and additionally the control device stops the air pump 58 and controls the pressure control valve 60 so that the pressing force HDP applied to the sensor 54 is decreased to atmospheric pressure. After SA9, the control device carries out the signal processing routine shown in FIG. 8.

Next, the signal processing routine of FIG. 8 will be explained. First, at SB1, the control device determines a peak pc of the one pulse of the carotid pulse wave wc represented by the pressure-pulse-wave signal SM2 read in at SA7 of FIG. 7, and a peak pb of the one pulse of the brachial pulse wave wb represented by the cuff-pulse-wave signal SM1 also read in at SA7 of FIG. 7, and stores, in the RAM 74, respective magnitudes of the peak pc of the carotid pulse wave wc and the peak pb of the brachial pulse wave wb.

Then, the control goes to SB2 corresponding to the incident-wave-peak determining means 86. At SB2, the control device subjects, to a fourth-order differentiation treatment or analysis, a portion or length of the pressure-pulse-wave signal SM2, read in at SA7 of FIG. 7, that continues from a rising point of the carotid pulse wave wc to the peak pc determined at SB1, and thereby determines an inflection point or a maximal point occurring to the length of the signal SM2. A time of occurrence of the inflection or maximal point is determined as a time of occurrence of a peak pci of the incident wave wci, and is stored in the RAM 74. In addition, a magnitude of the inflection or maximal point is stored, in the RAM 74, as a magnitude of the peak pci of the incident wave wci. Similarly, the control device determines a magnitude, and a time of occurrence, of a peak pbi of the incident wave wbi of the brachial pulse wave wb, and stores them in the RAM 74.

Then, the control goes to SB3 corresponding to the augmentation-index determining means 88. At SB3, the control device calculates a peak difference $\Delta Pc$ by subtracting the magnitude of the peak pci of the incident wave wci, determined at SB2, from the magnitude of the peak pc of the carotid pulse wave wc, determined at SB1. In addition, the control device calculates a carotid-pulse-wave augmentation index AIc (%) by substituting the thus obtained peak difference $\Delta P$, and the pulse pressure PPc as the magnitude of the peak pc of the carotid pulse wave wc, determined at SB1, for the corresponding variables of the above-indicated Expression 1. Similarly, the control device calculates a brachial-pulse-wave augmentation index AIb (%). Then, the control device controls the display device 76 to display the thus determined carotid-pulse-wave augmentation index AIc and brachial-pulse-wave augmentation index AIb, so that the two sorts of indexes AIc, AIb can be compared with each other by a medical person to evaluate arteriosclerosis of the subject. However, the flow chart of FIG. 8 additionally includes the following steps for automatically evaluating arteriosclerosis.

Then, the control goes to SB4 corresponding to the comparison-value calculating means 90. At SB4, the control device subtracts, from the carotid-pulse-wave augmentation index AIc determined at SB3, the brachial-pulse-wave augmentation index AIb also determined at SB3, and thereby determines an augmentation-index difference, $\Delta AI$, as a comparison value.

Subsequently, the control goes to SB5 corresponding to the arteriosclerosis evaluating means 92. At SB5, the control device judges whether the augmentation-index difference $\Delta AI$ determined at SB4 falls within a predetermined arteriosclerosis range which is considerably narrow and whose middle value is 0. If a positive judgment is made, the control device judges that the subject has arteriosclerosis; and if not, the control device judges that the subject does not have arteriosclerosis. In addition, the control device controls the display device 76 to display the result of evaluation of arteriosclerosis.

As is apparent from the foregoing description of the illustrated embodiment employing the flow charts of FIGS. 7 and 8, the control device 32 determines, at SB3 (the augmentation-index determining means 88), the respective augmentation indexes of the neck portion 38 and the upper arm 14, and evaluates, at SB5 (the arteriosclerosis evaluating means 92), arteriosclerosis of the subject, based on the augmentation-index difference $\Delta AI$ as the comparison value of the respective augmentation indexes AI of the neck portion 38 and the upper arm 14. Since the present apparatus 10 can evaluate arteriosclerosis of the subject by comparing two sorts of augmentation indexes AI obtained from the same subject, with each other, physiological changes and/or environmental influences of the augmentation indexes AI are offset. Therefore, the present apparatus 10 can evaluate arteriosclerosis with higher accuracy than an accuracy of evaluation of arteriosclerosis based on a single augmentation index AI.

In the illustrated embodiment employing the flow charts, the control device 32 determines, at SB3 (the augmentation-index determining means 88), the carotid-pulse-wave augmentation index AIc as the augmentation index AI of the neck portion 38 and the brachial-pulse-wave augmentation index AIb as the augmentation index AI of the upper arm 14, and controls the display device 76 to display the thus determined, two sorts of augmentation indexes AIc, AIb. Thus, a medical person can compare the two sorts of augmentation indexes AI with each other and judge that the nearer the two indexes are to each other, the higher degree of arteriosclerosis the subject has, i.e., that the remoter the two indexes are from each other, the lower degree of arteriosclerosis the subject has. Therefore, the present apparatus 10 can evaluate arteriosclerosis with higher accuracy than an accuracy of evaluation of arteriosclerosis based on a single augmentation index AI.

Next, there will be described another embodiment of the present invention. In the following description, the same reference numerals as used in the above-described, first embodiment are used to designate the corresponding elements of the present, second embodiment, and the description thereof is omitted.

Figure 9:
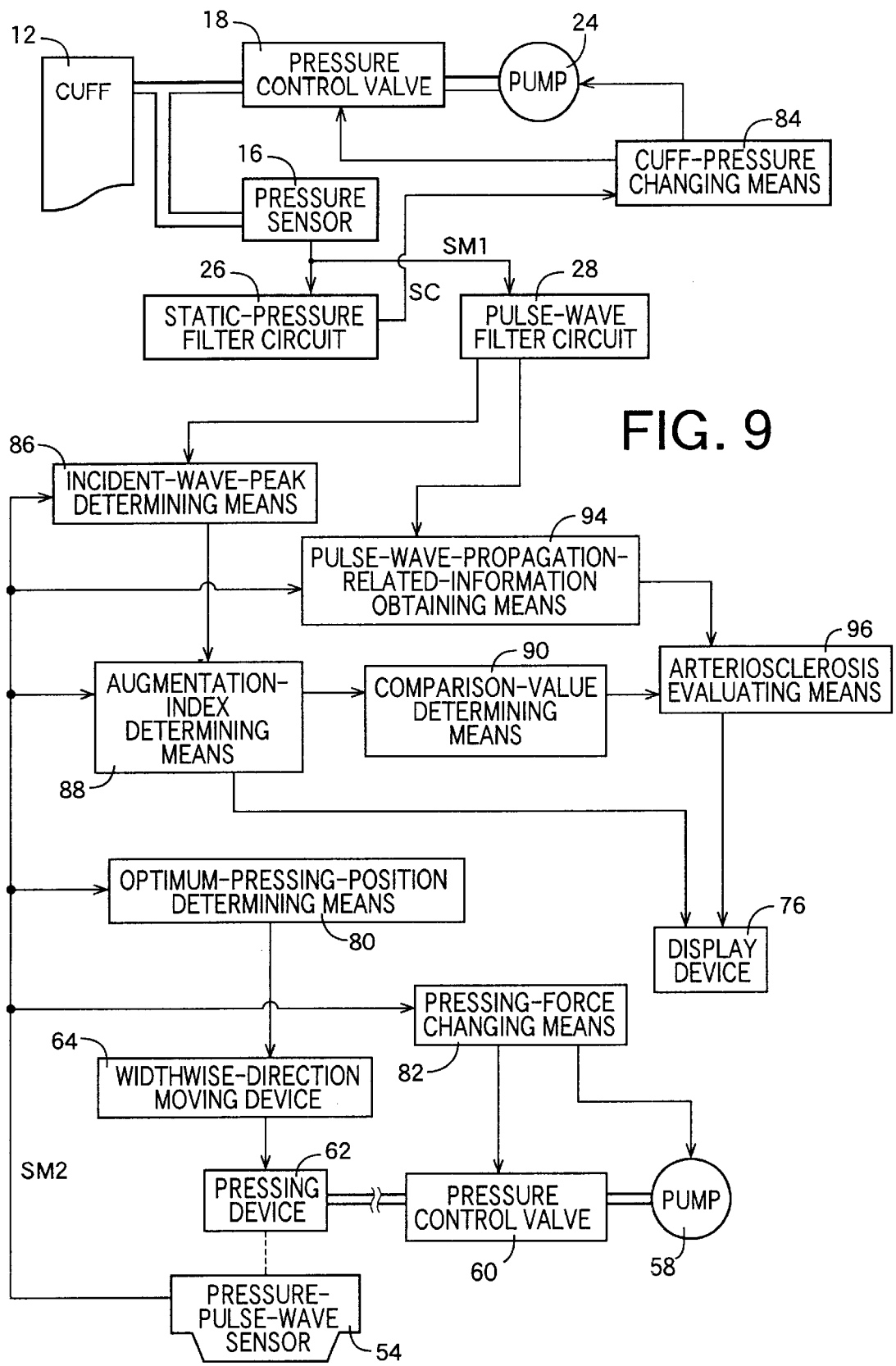
FIG. 9 is a block diagram for explaining essential control functions of an electronic control device of another arteriosclerosis evaluating apparatus as a second embodiment of the present invention.

FIG. 9 shows a block diagram for explaining essential control functions of the electronic control device 32 of an arteriosclerosis evaluating apparatus different from the first apparatus shown in FIG. 1. The present arteriosclerosis evaluating apparatus differs from the first apparatus, in that the present apparatus additionally includes an input device, not shown, and the control device 32 of the present apparatus has different control functions. The input device is operable by a person to input a height, H, of a patient, and supplies, in response to the operation, a signal, SH, representing the inputted patient's height H, to the control device 32. The control functions of the control device 32 of the present apparatus differ from those of the control device 32 of the first apparatus, in that the former control functions additionally include a pulse-wave-propagation-velocity-related-information obtaining means 94, and an arteriosclerosis evaluating means 96 different from the arteriosclerosis evaluating means 92 of the latter control functions. Hereinafter, there will be described the pulse-wave-propagation-velocity-related-information obtaining means 94 and the arteriosclerosis evaluating means 96.

The pulse-wave-propagation-velocity-related-information obtaining means 94 obtains, based on the cuff-pulse-wave signal SM1 extracted by the pulse-wave filter circuit 28 and the pressure-pulse-wave signal SM2 supplied by the pressure-pulse-wave sensor 54, a piece of pulse-wave-propagation-velocity-related information that is related to a velocity at which a pulse wave propagates through an artery of the patient.

More specifically described, the obtaining means 94 successively determines, as a pulse-wave propagation time DT (sec), a time difference between a time of occurrence of a prescribed point, such as a rising point or a peak, of each heartbeat-synchronous pulse of the brachial pulse wave wb represented by the cuff-pulse-wave signal SM1, and a time of occurrence of a prescribed point of a corresponding heartbeat-synchronous pulse of the carotid pulse wave wc represented by the pressure-pulse-wave signal SM2. In addition, the obtaining means 94 substitutes the patient's height H supplied from the input device, not shown, for a corresponding variable of the following Expression 2 representing a predetermined relationship between height H and propagation distance L, pre-stored in the ROM 72, thereby obtaining a propagation distance L, and additionally substitutes the thus obtained propagation distance L and the above-described pulse-wave propagation time DT for corresponding variables of the following Expression 3, thereby obtaining a pulse-wave propagation velocity PWV. The propagation distance L obtained according to Expression 2 means a difference between a length of an artery from the aorta to the position where the cuff 12 is worn, and a length of an artery from the aorta to the position where the probe 36 is worn:

$$L = \alpha H + \beta \quad \text{(Expression 2)}$$

($\alpha$ and $\beta$ are experimentally determined constants)

$$PWV = L/DT \quad \text{(Expression 3)}$$

The arteriosclerosis evaluating means 96 evaluates arteriosclerosis of the patient, based on the comparison value determined by the comparison-value calculating means 90 and the pulse-wave-propagation-velocity-related information obtained by the pulse-wave-propagation-velocity-related-information obtaining means 94, and controls the display device 76 to display the result of evaluation of arteriosclerosis. As previously described with respect to the arteriosclerosis evaluating means 92, the arteriosclerosis evaluating means 96 may judge whether the patient has arteriosclerosis or not, or may determine a degree of arteriosclerosis of the patient.

In the former case, the arteriosclerosis evaluating means 96 judges whether the patient has arteriosclerosis, as follows: In the first embodiment, the arteriosclerosis evaluating means 92 evaluates arteriosclerosis based on only the comparison value determined by the comparison-value calculating means 90. In this case, if the comparison value falls around a boundary between an arteriosclerosis arrange and a normal range, accuracy of evaluation of arteriosclerosis may not be sufficiently high. Hence, a gray range in which arteriosclerosis may not be sufficiently accurately evaluated based on a comparison value only, is determined in advance, and if the comparison value determined by the determining means 90 falls within the gray range, then the arteriosclerosis evaluating means 96 additionally refers to the pulse-wave-propagation-velocity-related information obtained by the pulse-wave-propagation-velocity-related-information obtaining means 94. If the pulse-wave-propagation-velocity-related information obtained indicates that the patient has arteriosclerosis, the evaluating means 96 judges that the patient has arteriosclerosis; and if the information obtained indicates that the patient does not have arteriosclerosis, the evaluating means 96 judges that the patient does not have arteriosclerosis.

In the above-indicated latter case, i.e., in the case where the arteriosclerosis evaluating means 96 determines a degree of arteriosclerosis of the patient, a relationship between pulse-wave-propagation-velocity-related information and arteriosclerosis degree is determined in advance and is stored in the ROM 72, and if the comparison value determined by the determining means 90 falls within the arteriosclerosis range, then the arteriosclerosis evaluating means 96 determines an arteriosclerosis degree based on the pulse-wave-propagation-velocity-related information actually obtained by the pulse-wave-propagation-velocity-related-information obtaining means 94, according to the relationship between pulse-wave-propagation-velocity-related information and arteriosclerosis degree. For example, in the case where the pulse-wave propagation velocity PWV is obtained as the pulse-wave-propagation-velocity-related information, a relationship between pulse-wave propagation velocity and arteriosclerosis degree is determined such that as the velocity PWV increases, the arteriosclerosis degree increases.

Figure 10:
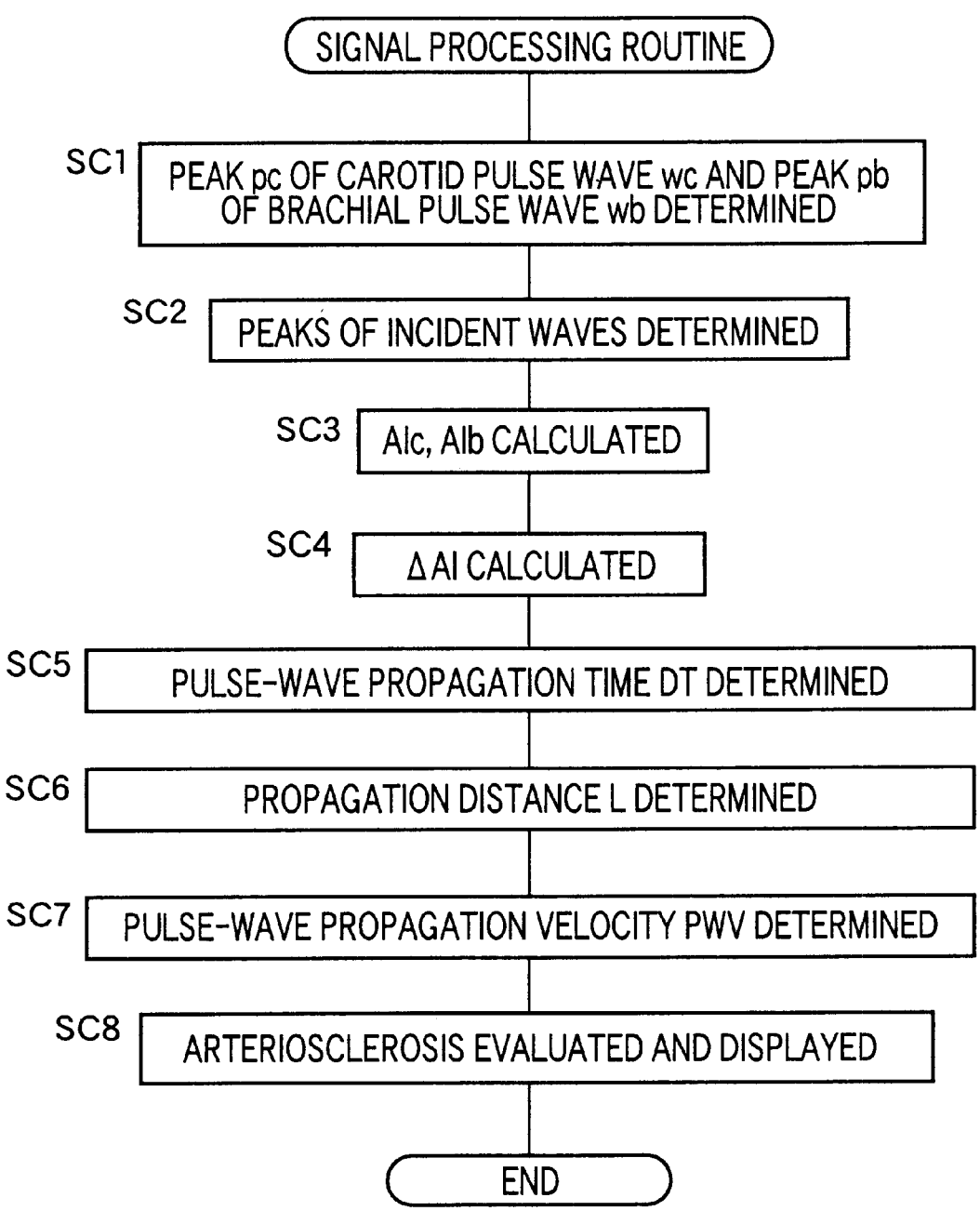
FIG. 10 is a flow chart for explaining more concretely control functions of a CPU of the control device, shown in FIG. 9, in particular, a signal processing routine.

FIG. 10 is a flow chart representing the control functions of the CPU 70, shown in FIG. 9, more particularly, a signal processing routine that corresponds to the signal processing routine shown in FIG. 8 and follows the signal reading routine shown in FIG. 7. The flow chart of FIG. 10 is executed after the signal SH representing the patient's height H is supplied from the input device, not shown.

At SC1 to SC4 of FIG. 10, the control device 32 performs the same operations as described above in connection with SB1 to SB4 of FIG. 8, respectively. After SC4, the control goes to SC5 to SC7 corresponding to the pulse-wave-propagation-velocity-related-information obtaining means 94. At SC5, the control device determines, as a pulse-wave propagation time DT, a time difference between a time of occurrence of the peak pc of the carotid pulse wave wc determined at SC1 and a time of occurrence of the peak pb of the brachial pulse wave wb also determined at SC1. Then, at SC6, the control device determines a propagation distance L, based on the patient's height input through the input device, according to the above-indicated Expression 2 and, at SC7, the control device determines a pulse-wave propagation velocity PW, based on the pulse-wave propagation time DT determined at SC5 and the propagation distance L determined at SC6, according to the above-indicated Expression 3. In addition, the control device controls the display device 76 to display the thus determined pulse-wave propagation velocity PWV together with the augmentation-index difference ΔAI.

Figure 11:
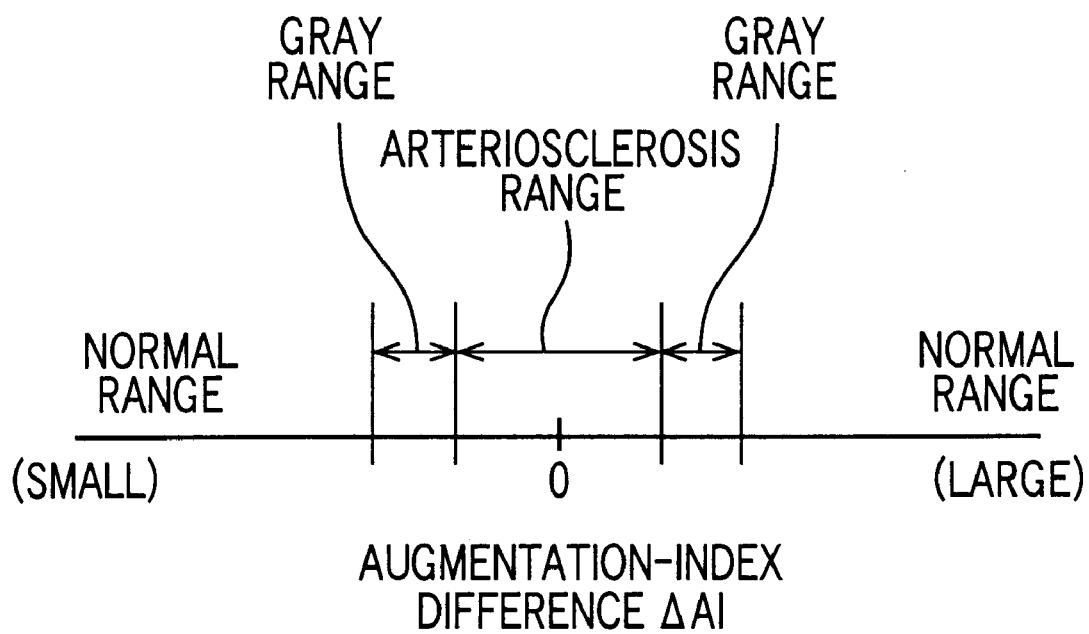
FIG. 11 is a relationship between augmentation index difference and arteriosclerosis, employed at Step SC8 of FIG. 10.

Then, the control goes to SC8 corresponding to the arteriosclerosis evaluating means 96. At SC8, first, the control device judges in which range the augmentation-index difference ΔAI calculated at SC4 falls, of a predetermined arteriosclerosis range, two normal ranges, and two gray ranges, shown in FIG. 11. The arteriosclerosis range is a considerably narrow range whose center is equal to zero; and the two gray range are provided between the arteriosclerosis range and the two normal ranges, respectively.

If the augmentation-index difference ΔAI falls in the arteriosclerosis range, the control device judges that the patient has arteriosclerosis; and if the augmentation-index difference ΔAI falls in one of the normal ranges, the control device judges that the patient does not have arteriosclerosis. On the other hand, if the augmentation-index difference ΔAI falls in one of the gray ranges, the control device additionally judges whether the pulse-wave propagation velocity PWV determined at SC7 falls in a predetermined abnormal range. If the pulse-wave propagation velocity PWV falls in the abnormal range, the control device judges that the patient has arteriosclerosis; and if not, the control device judges that the patient does not have arteriosclerosis. Then, the control device controls the display device 76 to display the result of judgment.

As is apparent from the foregoing description of the embodiment employing the flow chart of FIG. 10, the control device 32 evaluates, at SC8 (the arteriosclerosis evaluating means 96), arteriosclerosis of the patient based on not only the augmentation-index difference ΔAI as the comparison of the respective augmentation indexes AI of the neck portion 38 and the upper arm 14, but also the pulse-wave propagation velocity PWV that is, like the augmentation indexes AI, an index indicative of arteriosclerosis. Thus, the present apparatus can evaluate arteriosclerosis with improved accuracy.

While the present invention has been described in its preferred embodiments by reference to the drawings, it is to be understood that the invention may otherwise be embodied.

For example, since augmentation index AI changes in relation with arteriosclerosis, the arteriosclerosis evaluating means 96 employed in the second embodiment may be modified to evaluate arteriosclerosis based on not only the comparison value and but also the augmentation index AI, determined by the augmentation-index determining means 88, that replaces the pulse-wave-propagation-velocity-related information. Since the augmentation-index determining means 88 determines the two augmentation indexes AI, i.e., the carotid-pulse-wave augmentation index AIc and the brachial-pulse-wave augmentation index AIb, the evaluating means 96 may evaluate arteriosclerosis based on one of the two augmentation indexes AI, or an average of the two indexes.

In the above-described modified form of the second embodiment, the apparatus 10 can evaluate arteriosclerosis with improved accuracy, since the augmentation index AI is taken into account in addition to the comparison value as the comparison of the respective augmentation indexes AI of the neck portion 38 and the upper arm 14.

Pulse pressure PP also changes in relation with arteriosclerosis. As arteriosclerosis advances, the pulse pressure increases because, as the arteriosclerosis advances, the amount of expansion of blood vessels decreases, which results in decreasing the effect of attenuating the increasing of pressure caused by the ejection of blood from the heart. Therefore, the arteriosclerosis evaluating means 96 employed in the second embodiment may be modified to evaluate arteriosclerosis based on not only the comparison value and but also the pulse pressure PP that replaces the pulse-wave-propagation-velocity-related information obtained by the pulse-wave-propagation-velocity-related-information obtaining means 94. The augmentation-index determining means 88 functions as a pulse-pressure determining means for determining at least one of the pulse pressure PPc of the carotid pulse wave wc and the pulse pressure PPb of the brachial pulse wave wb. In the case where the pulse-pressure determining means determines the two pulse pressures PP, i.e., the pulse pressure PPc of the carotid pulse wave wc and the pulse pressure PPb of the brachial pulse wave wb, the arteriosclerosis evaluating means 96 may evaluate arteriosclerosis based on one of the two pulse pressures PP or an average of the two pulse pressures.

In the above-described, another modified form of the second embodiment, the apparatus 10 can evaluate arteriosclerosis with improved accuracy, since the pulse pressure PP is taken into account in addition to the comparison value as the comparison of the respective augmentation indexes AI of the neck portion 38 and the upper arm 14.

The arteriosclerosis evaluating apparatus 10 employs the two pulse-wave detecting devices, i.e., the brachial-pulse-wave detecting device 35 and the carotid-pulse-wave detecting device (the pressure-pulse-wave detecting probe) 36. However, the two pulse-wave detecting devices may be replaced with a single pulse-wave detecting device which can be worn on each of a plurality of different portions of the subject or patient to detect a pulse wave from the each of those portions. Otherwise, the two pulse-wave detecting devices may be replaced with three or more pulse-wave detecting devices.

In the case where three or more pulse waves are detected from three or more different portions of a living subject, the comparison-value calculating means 88 may be modified to determine a comparison value based on each of all possible combinations of two pulse waves selected from the three or more pulse waves, and the arteriosclerosis evaluating means 92 may be modified to evaluate arteriosclerosis based on an average of all the thus obtained comparison values. The three or more different portions of the subject may include not only the upper arm 14 and/or the neck portion 38 but also a wrist, a femoral portion, and/or an ankle.

In the illustrated embodiment, the comparison-value calculating means 90 calculates the comparison value of the two augmentation indexes AI, and the arteriosclerosis evaluating means 92 evaluates arteriosclerosis based on the comparison value calculated by the comparison-value calculating means 90. However, the ROM 72 may be modified to store a map representing a predetermined relationship between two augmentation indexes AI and arteriosclerosis. In this case, the arteriosclerosis evaluating means 92 may be modified to evaluate directly arteriosclerosis, based on the two augmentation indexes AI actually determined by the augmentation-index determining means 88, according to the map stored in the ROM 72.

The present invention may be embodied with other various changes without departing from the spirit of the invention.

What is claimed is:

1. An apparatus for evaluating arteriosclerosis of a living subject, comprising:

a pulse-wave detecting device which detects a pulse wave from each of a first portion and a second portion of the subject, each of the respective pulse waves detected from the first and second portions containing an incident-wave component;

an augmentation-index determining means for determining, based on the pulse wave detected from the first portion by the pulse-wave detecting device, a first augmentation index indicative of a degree of augmentation of an amplitude of the pulse wave detected from the first portion, from an amplitude of the incident-wave component of the pulse wave detected from the first portion, and determining, based on the pulse wave detected from the second portion by the pulse-wave detecting device, a second augmentation index indicative of a degree of augmentation of an amplitude of the pulse wave detected from the second portion, from an amplitude of the incident-wave component of the pulse wave detected from the second portion; and an arteriosclerosis evaluating means for evaluating the arteriosclerosis of the subject, based on a comparison of the first and second augmentation indexes determined by the augmentation-index determining means.

2. An apparatus according to claim 1, further comprising a comparison-value calculating means for calculating a comparison value as the comparison of the first and second augmentation indexes determined by the augmentation-index determining means, wherein the arteriosclerosis evaluating means evaluates the arteriosclerosis of the subject, based on the comparison value calculated by the comparison-value calculating means and at least one of the first and second augmentation indexes determined by the augmentation-index determining means.

3. An apparatus according to claim 1, further comprising:

a comparison-value calculating means for calculating a comparison value as the comparison of the first and second augmentation indexes determined by the augmentation-index determining means; and a pulse-wave-propagation-velocity-related-information obtaining device which obtains pulse-wave-propagation-velocity-related information that is related to a velocity at which the pulse wave propagates in the subject, wherein the arteriosclerosis evaluating means evaluates the arteriosclerosis of the subject, based on the comparison value calculated by the comparison-value calculating means and the pulse-wave-propagation-velocity-related information obtained by the pulse-wave-propagation-velocity-related-information obtaining device.

4. An apparatus according to claim 1, further comprising:

a comparison-value calculating means for calculating a comparison value as the comparison of the first and second augmentation indexes determined by the augmentation-index determining means; and a pulse-pressure determining means for determining a pulse pressure of at least one of the respective pulse waves detected from the first and second portions by the pulse-wave detecting device, wherein the arteriosclerosis evaluating means evaluates the arteriosclerosis of the subject, based on the comparison value calculated by the comparison-value calculating means and the pulse pressure determined by the pulse-pressure determining means.

5. An apparatus according to claim 1, wherein the augmentation-index determining means determines, based on the pulse wave detected as a first pulse wave from the first portion by the pulse-wave detecting device, the first augmentation index, AIc, equal to a percentage of a difference, $\Delta Pc$, of a pulse pressure, PPc, of the first pulse wave from a pulse pressure PPci of the incident-wave component of the first pulse wave, relative to the pulse pressure PPc of the first pulse wave, according to a following expression: $AIc=(\Delta Pc/PPc)\times 100$, and determines, based on the pulse wave detected as a second pulse wave from the second portion by the pulse-wave detecting device, the second augmentation index, AIb, equal to a percentage of a difference, $\Delta Pb$, of a pulse pressure, PPb, of the second pulse wave from a pulse pressure PPbi of the incident-wave component of the second pulse wave, relative to the pulse pressure PPb of the second pulse wave, according to a following expression: $AIb=(\Delta Pb/PPb)\times 100$.

6. An apparatus according to claim 5, further comprising a comparison-value calculating means for calculating, as the comparison of the first and second augmentation indexes AIc, AIb determined by the augmentation-index determining means, a comparison value selected from the group consisting of a ratio, R, of one of the first and second indexes AIc, AIb to the other index; a difference, d, of one of the first and second indexes AIc, AIb from the other index; and a value obtained by dividing the difference d by the ratio R.

7. An apparatus according to claim 3, wherein the pulse-wave detecting device comprises:

a pressure-pulse-wave sensor which is adapted to be pressed against an artery of the first portion of the subject to detect, from the first portion, a pressure pulse wave produced from the artery; and an inflatable cuff which is adapted to be worn on the second portion of the subject to detect, from the second portion, a cuff pulse wave.

8. An apparatus according to claim 7, wherein the pulse-wave-propagation-velocity-related-information obtaining device comprises time-difference determining means for determining, as the pulse-wave-propagation-velocity-related information, a time difference between a time of occurrence of a prescribed point of a heartbeat-synchronous pulse of the pressure pulse wave detected by the pressure-pulse-wave sensor and a time of occurrence of a prescribed point of a corresponding heartbeat-synchronous pulse of the cuff pulse wave detected by the cuff.

9. An apparatus according to claim 8, wherein the pulse-wave-propagation-velocity-related-information obtaining device further comprises:

a propagation-distance determining means for determining a propagation distance equal to a difference of a first distance between the first portion, and a heart, of the subject and a second distance between the second portion, and the heart, of the subject; and a velocity determining means for determining, as the pulse-wave-propagation-velocity-related information, the velocity based on the time difference determined by the time-difference determining means and the propagation distance determined by the propagation-distance determining means.

10. An apparatus for evaluating arteriosclerosis of a living subject, comprising:

a pulse-wave detecting device which detects a pulse wave from each of a first portion and a second portion of the subject, each of the respective pulse waves detected from the first and second portions containing an incident-wave component;

an augmentation-index determining means for determining, based on the pulse wave detected from the first portion by the pulse-wave detecting device, a first augmentation index indicative of a degree of augmentation of an amplitude of the pulse wave detected from the first portion, from an amplitude of the incident-wave component of the pulse wave detected from the first portion, and determining, based on the pulse wave detected from the second portion by the pulse-wave detecting device, a second augmentation index indicative of a degree of augmentation of an amplitude of the pulse wave detected from the second portion, from an amplitude of the incident-wave component of the pulse wave detected from the second portion; and a display device which displays the first and second augmentation indexes determined by the augmentation-index determining means.

* * * * *